(12) United States Patent
Uhde et al.

(10) Patent No.: US 8,126,111 B2
(45) Date of Patent: Feb. 28, 2012

(54) DISPLAYING RECORDINGS IN A SUPERIMPOSED OR ORIENTED WAY

(75) Inventors: Jorg Uhde, Munich (DE); Aleksander Bogojevic, Munich (DE)

(73) Assignee: Brainlab AG, Feldkirchen (DE)

(*) Notice: Subject to any disclaimer, the term of this patent is extended or adjusted under 35 U.S.C. 154(b) by 251 days.

(21) Appl. No.: 12/357,537

(22) Filed: Jan. 22, 2009

(65) Prior Publication Data

US 2009/0207971 A1    Aug. 20, 2009

(30) Foreign Application Priority Data

Jan. 22, 2008  (EP) .................................... 08150480
Sep. 22, 2008  (EP) .................................... 08164757

(51) Int. Cl.
*A61B 6/02* (2006.01)
*G03C 9/00* (2006.01)
*G01N 23/083* (2006.01)

(52) U.S. Cl. .......... 378/41; 378/62; 378/98.12; 378/205
(58) Field of Classification Search .................... 378/41, 378/62, 63, 91, 98, 98.2, 98.3, 98.5, 98.8, 378/98.12, 205, 210; 359/13
See application file for complete search history.

(56) References Cited

U.S. PATENT DOCUMENTS 5,247,555 A * 9/1993 Moore et al. ...................... 378/4
(Continued)

FOREIGN PATENT DOCUMENTS

DE          10015815        10/2001
(Continued)

*Primary Examiner* — Anastasia Midkiff
(74) *Attorney, Agent, or Firm* — Renner, Otto, Boisselle & Sklar, LLP (57) ABSTRACT

A method for the superimposed depiction, on at least one screen, of overlapping recordings of a region to be imaged which is recorded in at least two recording steps, wherein multiple markers are fixedly provided in the region to be imaged, such that at least two recordings can be spatially produced, offset with respect to the markers, using an x-ray apparatus, wherein the recordings are registered relative to the marker, and the image data of accordingly registered recordings is mutually oriented by means of a common imaging protocol and depicted on the at least one screen in a superimposed way.

30 Claims, 4 Drawing Sheets

U.S. PATENT DOCUMENTS

| | | | |
|---|---|---|---|
| 5,841,148 A * | 11/1998 | Some et al. | 250/584 |
| 6,491,429 B1 * | 12/2002 | Suhm | 378/205 |
| 6,516,046 B1 * | 2/2003 | Frohlich et al. | 378/65 |
| 6,535,574 B1 * | 3/2003 | Collins et al. | 378/65 |
| 6,697,664 B2 * | 2/2004 | Kienzle, III et al. | 600/427 |
| 6,771,734 B2 * | 8/2004 | Hebecker et al. | 378/8 |
| 6,814,489 B2 * | 11/2004 | Jensen et al. | 378/197 |
| 7,505,559 B2 * | 3/2009 | Kuduvalli | 378/65 |
| 7,519,415 B2 * | 4/2009 | Mitschke et al. | 600/424 |
| 2001/0053204 A1 * | 12/2001 | Navab et al. | 378/205 |
| 2002/0018588 A1 | 2/2002 | Kusch | |
| 2003/0179856 A1 | 9/2003 | Mitsch | |
| 2004/0077942 A1 | 4/2004 | Hall et al. | |
| 2005/0004449 A1 | 1/2005 | Mitsch et al. | |
| 2005/0163279 A1 | 7/2005 | Mitscke et al. | |
| 2005/0207529 A1 * | 9/2005 | Boese et al. | 378/41 |
| 2007/0140438 A1 | 6/2007 | Horndler et al. | |

FOREIGN PATENT DOCUMENTS

| | | |
|---|---|---|
| DE | 10210645 | 10/2003 |
| DE | 10322739 | 12/2004 |
| DE | 10360025 | 7/2005 |
| EP | 1782734 | 9/2007 |

* cited by examiner

DISPLAYING RECORDINGS IN A SUPERIMPOSED OR ORIENTED WAY

This application claims priority of European Patent Application No. 08 150 480.5 filed Jan. 22, 2008 and European Patent Application No. 08 164 757.0 filed Sep. 22, 2008, which applications are hereby incorporated herein in their entirety. In addition, a copy of European Patent Application No. 08 164 757.0 is appended hereto as Appendix A and forms a part of this application.

FIELD OF THE INVENTION

The invention relates to a method for the oriented, superimposed depiction, on at least one screen, of preferably overlapping recordings of a region to be imaged which is recorded in at least two recording steps using a navigation system. The invention also relates to a method for the oriented depiction, on at least one screen, of recordings of a region to be imaged which is recorded in at least two recording steps, wherein the recordings can be localized in a common coordinate system of the region to be imaged, wherein the navigation system comprises the following features:
- an x-ray detector comprising an x-ray source which is arranged opposite it, which can be jointly moved with respect to each other and with respect to the region to be imaged, in a relationship which can be predetermined;
- a stereo recording system, for instance a stereo camera;
- multiple marker devices which are assigned to the x-ray detector and the region to be imaged, and which can be at least partially detected by the stereo recording system;

wherein the method comprises the following steps:
- a) a first recording of the region to be imaged is initiated by the x-ray apparatus in a first position, wherein a first control signal is output;
- b) the first control signal causes the stereo recording system to detect first positions of the multiple marker devices on the x-ray detector and the region to be imaged;
- c) data concerning the first positions is stored;
- d) the data concerning the first positions is correlated, with computer assistance, with image points of the x-ray recording, in order to register the x-ray recording;
- e) the x-ray detector is moved, together with the x-ray source, relative to the region to be imaged into a second position;
- f) a second recording is initiated by the x-ray detector, wherein a second control signal is output;
- g) the second control signal causes the stereo recording system to detect second positions of the marker devices on the x-ray detector and the region to be imaged;
- h) data concerning the second positions is correlated, with computer assistance, with image points of the x-ray recording, in order to register the second x-ray recording;
- i) via the common coordinate system of the region to be imaged, a transformation matrix for the change in the position of the x-ray detector between the first and second recording is determined;
- j) the recordings are oriented and scaled with respect to each other using the matrix, wherein a true-to-scale scale of magnitude is determined from the change in position in the z direction, a true-to-scale distance between the recordings is determined from a change in position in the x and/or y direction, a true-to-scale rotation is determined from an angle $\Omega$, and a true-to-scale tilt of the second recording with respect to the plane of the first recording is determined from angles $\Theta$ and $\phi$;
- k) the recordings are oriented with respect to each other using the determined values, and displayed.

In particular, a method is proposed for displaying recordings of a patient's body region, produced by means of x-raying, such that they are oriented with respect to each other and overlap, in particular with a maximum of image information, for the purpose of computer-assisted navigation.

In particular, a method is proposed for orienting, with respect to each other, recordings of a patient's body region, produced by means of x-raying, for the purpose of computer-assisted navigation.

BACKGROUND

In order to obtain informative images with regard to body parts of a human or animal, for example for orthopedics or traumatology, it is common to take for example two recordings of a body region, i.e. for instance an anatomical structure, using an x-ray apparatus.

The at least two x-ray recordings are obtained by spatially displacing the x-ray apparatus relative to the region of the patient to be recorded.

Multiple recordings are then usually imaged on two separate monitors. One very common configuration is a mobile x-ray apparatus, also referred to as a "C-arm", in conjunction with two monitors, wherein a current image is displayed on one monitor, and any previously recorded image of the body region of interest, which can be replaced with the current image at any time, is displayed on another monitor. One problem with this is that the images do not have a defined orientation, scaled relationship or the like with respect to each other, i.e. the displayed images may be tilted in any spatial directions with respect to each other, and joining the images to each other or displaying them to the same scale is not systematically possible.

Figure 3:
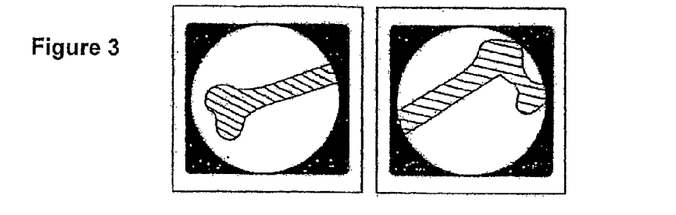
FIG. 3 shows an anatomical structure according to FIG. 1a, in two non-oriented representations on a screen (navigation, data processing) in accordance with the prior art.

FIG. 3 depicts an anatomical structure—in this case, a femur—which has been recorded in two recordings using a C-arm, at different positions along a patient's body. These two recordings or x-ray images of the anatomical structure are displayed on two monitors of the C-arm. As can be seen, the portions of the anatomical structure in accordance with FIG. 1a as displayed on the different monitors have different alignments and image magnifications, as can be seen from FIG. 3. A reproducible and realistic orientation is not possible on the basis of this screen content in accordance with FIG. 3.

Figure 8A:
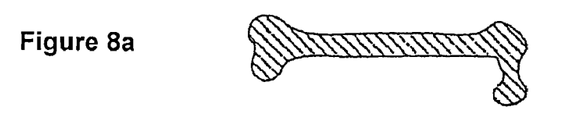
FIGS. 8a and 8b show an anatomical structure in its original form (FIG. 8a) and on the basis of two recordings on two screens (C-arm) or in two non-oriented representations on one screen (navigation, data processing) (FIG. 8b) in accordance with the prior art.
Figure 8B:
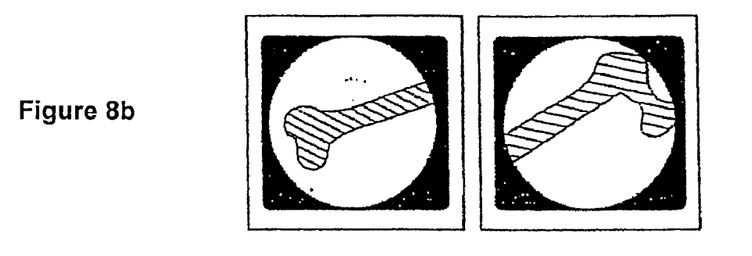

FIG. 8b depicts an anatomical structure—in this case, a hip bone—which has been recorded in two recordings using a C-arm, at different positions along a patient's body. These two recordings or x-ray images of the anatomical structure are displayed on two monitors of the C-arm. As can be seen, the portions of the anatomical structure in accordance with FIG. 8a as displayed on the different monitors have different alignments and image magnifications, as can be seen from FIG. 8b. A reproducible and realistic orientation is not possible on the basis of this screen content in accordance with FIG. 8b.

SUMMARY OF THE INVENTION

One aim relative to the prior art may be viewed as being that of three-dimensionally navigating in or on a patient's body in order to reach an anatomical structure in an operation. To this end, it is preferable to produce two or more x-ray recordings for navigation which overlap as exactly as possible and the overlap geometry of which should be definably known. The central rays of said x-ray recordings should exhibit as exact a point of intersection as possible. The arrangement of the multiple overlapping x-ray recordings results in positional information in three dimensions, wherein information for a spatial representation with a minimum of imaging errors can be gathered from two x-ray recordings which have been recorded as perpendicular to each other as possible. The fact that the x-ray recordings have to overlap each other reduces the effective imaging range within which it is possible to navigate with full three-dimensional information. Reference may be made in this respect to FIG. 4, which shows a radioscopic image 1 which lies in the plane of the sheet of paper of FIG. 4. Another radioscopic image region 2 lies perpendicular to the radioscopic image 1, wherein an exact overlap cannot be identified. The usable region for navigation which results from these two images 1, 2 is indicated by cross-hatching. As can be seen, the usable image diameter on the basis of two radioscopic images is at best as large as the diameter of one radioscopic image and is generally even smaller.

The present invention also enables the oriented depiction, on at least one screen, of recordings of a region to be imaged which is recorded in at least two recording steps. The intention is in particular to enable images recorded in multiple recordings to be systematically adapted to each other and/or placed onto each other or combined in an oriented way, and in particular to enable these recordings which are oriented with respect to each other or combined in an oriented way to be subsequently used for navigation.

For the intention is in particular to be able to subsequently use a recording of an overlapping region, which is combined in an oriented way, in order to increase the effective three-dimensional region which can be used for navigation.

The invention also enables three-dimensionally navigating in or on a patient's body in order for instance to place a probe or to treat an anatomical structure. To this end, it is preferable to produce two or more x-ray recordings for navigation which overlap as exactly as possible and the overlap geometry of which should be definably known. The central rays of said x-ray recordings should exhibit as exact a point of intersection as possible. The arrangement of the multiple overlapping x-ray recordings results in positional information in three dimensions, wherein information for a spatial representation with a minimum of imaging errors can be gathered from two x-ray recordings which have been recorded as perpendicular to each other as possible. The fact that the x-ray recordings should overlap each other reduces the effective imaging range within which it is possible to navigate with full three-dimensional information. Reference may be made in this respect to FIG. 10, which shows a radioscopic image 1 which lies in the plane of the sheet of paper of FIG. 10. Another radioscopic image region 2 lies perpendicular to the radioscopic image 1, wherein an exact overlap cannot be identified. The usable region for navigation which results from these two images 1, 2 is indicated by cross-hatching. As can be seen, the usable image diameter on the basis of two radioscopic images is at best as large as the diameter of one radioscopic image and is generally even smaller.

The advantages which may be achieved in accordance with one aspect (the first aspect) of the invention are based on a method for the oriented depiction of in particular overlapping recordings of a region—in particular of an anatomical structure—to be imaged which is recorded in at least two recording steps using a navigation system comprising the following features:

an x-ray detector comprising an x-ray source which is arranged opposite it, which can be jointly moved with respect to each other and with respect to the region to be imaged, in a relationship which can be predetermined;

a stereo recording system, for instance a stereo camera;

multiple marker devices which are assigned to the x-ray detector and the region to be imaged, and which can be at least partially detected by the stereo recording system;

wherein the method comprises the following steps:

a) a first recording of the region to be imaged is initiated by the x-ray apparatus in a first position, wherein a first control signal is output;

b) the first control signal causes the stereo recording system to detect first marker positions of the multiple marker devices on the x-ray detector and the region to be imaged;

c) data concerning the first marker positions is stored;

d) the data concerning the first marker positions is correlated, with computer assistance, with image points of the x-ray recording, in order to register the x-ray recording;

e) a first position (S) of the x-ray source relative to the detector is ascertained and stored;

f) with the aid of the registration, the position of the source in the coordinate system of the region to be imaged is determined and stored;

g) the x-ray detector is moved, together with the x-ray source, relative to the region to be imaged into a second position (S') for a second recording, wherein changes in the position of the detector are detected during the movement, and a second position of the source is determined by means of the first relative position;

h) a second recording is initiated at the second position, wherein a second control signal is output;

i) the second control signal causes the stereo recording system to detect second marker positions of the marker devices on the x-ray detector and the region to be imaged;

j) the data concerning the second marker positions is correlated, with computer assistance, with image points of the x-ray recording, in order to register the second x-ray recording;

k) an additional position is ascertained from the second position (S') and the first position (S);

l) by means of the additional position (<S>), the recordings are registered and displayed in a superimposed way.

The method in accordance with the invention is preferably achieved by moving the x-ray detector on a spherical shell around the x-ray source. If it is possible to ideally or almost ideally realize this method variant, two or more x-ray recordings of an anatomical object, for instance a bone, can be oriented with respect to each other and correspondingly depicted to a high level of accuracy, since the geometry of the imaging cone between the x-ray source and the x-ray detector, in conjunction with the stereo recording system, is defined exactly enough that the image points of the x-ray recordings can be exactly or at least almost exactly oriented with respect to each other, adapted to scale, etc. using a definitive assignment protocol.

The advantages which may be achieved in accordance with another aspect (the second aspect) of the invention are based on a method for the oriented depiction of recordings of a region—in particular of an anatomical structure—to be imaged which is recorded in at least two recording steps using a navigation system, wherein the recordings can be localized in a common coordinate system of the region to be imaged, wherein the navigation system comprises the following features:

an x-ray detector comprising an x-ray source which is arranged opposite it, which can be jointly moved with respect to each other and with respect to the region to be imaged, in a relationship which can be predetermined;
a stereo recording system, for instance a stereo camera;
multiple marker devices which are assigned to the x-ray cone and the region to be imaged, and which can be at least partially detected by the stereo recording system;
wherein the method comprises the following steps:
  a) a first recording of the region to be imaged is initiated by the x-ray apparatus in a first position, wherein a first control signal is output;
  b) the first control signal causes the stereo recording system to detect first positions of the multiple marker devices on the x-ray detector and the region to be imaged;
  c) data concerning the first positions is stored;
  d) the data concerning the first positions is correlated, with computer assistance, with image points of the x-ray recording, in order to register the x-ray recording;
  e) the x-ray detector is moved, together with the x-ray source, relative to the region to be imaged into a second position;
  f) a second recording is initiated by the x-ray detector, wherein a second control signal is output;
  g) the second control signal causes the stereo recording system to detect second positions of the marker devices on the x-ray detector and the region to be imaged;
  h) data concerning the second positions is correlated, with computer assistance, with image points of the x-ray recording, in order to register the second x-ray recording;
  i) via the common coordinate system of the region to be imaged, a transformation matrix for the change in the position of the x-ray cone between the first and second recording is determined;
  j) the recordings are oriented and scaled with respect to each other using the matrix, wherein a true-to-scale scale of magnitude is determined from the change in position in the z direction, a true-to-scale distance between the recordings is determined from a change in position in the x and/or y direction, a true-to-scale rotation is determined from an angle $\Omega$, and a true-to-scale tilt of the second recording with respect to the plane of the first recording is determined from angles $\Theta$ and $\phi$;
  k) the recordings are oriented with respect to each other using the determined values, and displayed.

Expedient method variants of the method in accordance with the invention may be gathered from the sub-claims.

Advantageously, at least two recordings are produced in at least approximately the same plane. By recording two radioscopic and/or x-ray images in at least approximately the same plane, it is possible to enable a similarity between the positions of the x-ray source during the recordings to be established.

The methods in accordance with the invention are accompanied by the use of a navigation system comprising a stereo recording system, generally a stereo camera, wherein for example markers are arranged in a predetermined way on the x-ray detector and the region to be imaged and can be assigned to spatial coordinates by the navigation system, for instance by using a calibration. When a recording is taken, the stereo recording system is actuated at the same time as said x-ray recording, in order to obtain data concerning the spatial relationship between the x-ray recording and the region to be imaged. The navigation system detects and stores the current positions of the x-ray unit, which comprises the x-ray source and the x-ray detector, and of the markers provided on the region to be imaged, which are identified by the navigation system. Using subsequent data processing, the position of the x-ray source and the distortion in the image of the region to be imaged is ascertained from the spatial position of the detector and from the distorted arrangement of a number of the identified markers, whose actual position with respect to each other is known. Each position in the coordinate system of the region to be imaged and/or of the anatomical object is then assigned a projected point of the displayed x-ray image, wherein the projection lines proceed from the relative position which the x-ray source has in relation to the region to be imaged, at the time of recording.

Advantageous embodiments of the first aspect of the invention are discussed below.

In order to enable adjustment steps, so as to result in no change or as little change as possible in the location of the x-ray source between consecutive recordings, the stereo recording system is used in accordance with a preferred embodiment to indicate the positioning steps which the x-ray detector has to undergo in order for a second source position of the x-ray source for producing the second recording to deviate only slightly from the first source position or to correspond to it.

It should be noted here that the recordings cannot simply be cohered for example by geometric distortions in the image material, since the exact three-dimensional one-to-one assignment between rays in the object space and imaging points would then be annulled, and at least two image points would always be assigned to each object point, which would for example mean that a third navigated object introduced, such as for example a pointer, would be displayed twice or elongated and/or compressed in the overlap region of the images.

Positioning for the x-ray source can also be automatically corrected if the recording array for performing the method in accordance with the invention comprises a motorized or mechanically limiting array which automatically implements the positioning steps or optimizes the position of the x-ray source relative to the previous position of the x-ray source as the previous x-ray recording was being taken, wherein the subsequent and/or second x-ray recording could be taken with as small an adjustment in the position of the x-ray source as possible.

In general, displaying the different image points of the x-ray recordings relative to a common reference point in a coordinated way, while taking into account the distortions in the x-ray recordings relative to the reference point, enables the x-ray recordings and/or regions to be imaged to be depicted cohesively, oriented with respect to each other and adapted to scale, in particular in order to use these recordings for navigation.

Two or more such combined recordings of an overlapping region, which are as perpendicular to each other as possible or at least adopt an angle other than zero, can in particular be used in order to navigate with full three-dimensional information on a continuous region which is significantly larger than the image range of an x-ray apparatus.

In accordance with the method in accordance with the invention, an x-ray image of an object to be recorded can be registered to assigned marker positions by the navigation system and adduced as a reference image for one or more subsequent x-ray recordings. The x-ray detector is then moved out of a first position, along the surface of a spherical shell, wherein the x-ray source lies in the centre of the spherical shell, wherein the relative positions of the x-ray detector and the x-ray source are known due to the spatial information obtained during the first recording, wherein said information has also been rectified on the basis of the previously disclosed calibration. It is then essential that the x-ray detector is moved into a second position such that the new position of the x-ray source coincides with the old position, or such that a deviation between the position of the x-ray source during the first recording and the position of the x-ray source during the second recording does not exceed a particular deviation. Advantageously, a deviation of an order of magnitude of a few centimeters, in particular 1 cm or less, is tolerable. If it is possible to make the positions of the x-ray source during the first and second recording correspond, then an ideal imaging protocol can be realized. If a tolerable difference in position between the position of the x-ray source during the first recording and the position of the x-ray source during the second recording has been established, a suitable third and/or subsequent source position is calculated from the two source positions which is in particular the averaged source position or can for example also be an average source position which is weighed using the individual imaging errors. Proceeding from this calculated third and/or subsequent source position, it is likewise possible to calculate an imaging protocol for both projection cones and therefore for both x-ray recordings. The image information of the x-ray images can then be mutually adapted in terms of its scale, orientation and any other parameters for accurate imaging and depicted with as great a content of information as possible.

The recordings advantageously overlap. If the recordings do not overlap, an undetected region between the recordings is not displayed or is for example displayed in black. The undetected region can also be filled by taking one or more additional recordings. Directly consecutive recordings which do not exhibit an overlap can also be processed in accordance with the invention, since this is also enabled by preparing a source position, wherein the recordings are enabled by means of a source position, wherein the recordings can be rotated in a spherical shell about the source position common to the recordings.

In order to prepare additional image information and/or orientation information for a surgeon and/or physician, it is preferred—after a first and second recording have been produced in accordance with the invention—for the x-ray apparatus to be moved into a different position, in which to again record at least one recording or two recordings in accordance with the method in accordance with the invention at a different angle to the region to be imaged, wherein it is particularly advantageous if the second set of a first recording and second recording have been acquired at a particular angle, preferably 90°, to the first set of a first recording and second recording, since optimized spatial image information can thus be obtained. It is, however, also possible to proceed from small angles in accordance with the invention, for instance from a minimum angle of at least about 30°, but preferably from an angle of about 60°, wherein it is particularly advantageous if the second set of a first recording and second recording has been acquired at a particular angle, preferably 90°, typically greater than 60° or greater than 30°, to the first set of a first recording and second recording. The respectively overlapping recordings of the two sets of recordings which may be distanced from each other and/or are recorded at an angle to each other can then be registered and oriented with respect to each other in accordance with the invention, in order to be combined to form one or more cohesive images on one or more screen regions or screens, wherein spatial assignments between the image information of the x-ray recordings are computationally produced by means of the stereo camera and the markers detected by it.

Advantageous embodiments of the second aspect of the invention are discussed below.

It is advantageous if a selectable section of the recording range, i.e. an individual recording, is depicted parallel to the surface of the screen, i.e. a selected region is rotated and/or transformed into the surface of the screen, in order to be displayed in parallel, while other sections adjacent to the selected section are depicted passing into and/or out of the surface of the screen, in accordance with their orientation. In order to make the orientation of the different image sections with respect to each other more easily visible to the observer, the regions which are adjacent to the selected section can be made clearly identifiable on the screen, offset by an identifiable edge or edges and/or a two-dimensional marking such as for instance hatching, shading or the like.

By means of the present invention, it is then possible in a preferred embodiment to display two or more radioscopic images simultaneously, in a correct orientation and true-to-scale with respect to each other.

The registered x-ray recordings can be adapted to each other, and/or the first x-ray recording—which can serve as the reference image—can be adapted to the second x-ray recording, using the following algorithm and/or method, wherein this is to be regarded merely as an example. There are of course other approximation algorithms which have the result that the second x-ray image can be displayed on one or more screens in such a way that it is matched to the first x-ray image and/or to the reference image in terms of its size, distance, rotation and tilt.

X-ray images, as a kind of silhouette without depth information, can be assumed to be lying in three-dimensional space in the image intensifier, without loss of generality:

$$R^i(x_B^i) = E_B^i$$

wherein $x_B^i$ is the spatial points in the coordinate system of the image intensifier, $E_B^i$ is the possible planes of intersection (perpendicular to the central ray) through the ray cone, which contain the rectified image information of the x-ray image and lie at the location of the image intensifier, and R is an imaging protocol which describes the location of $E_B^i$ at which a spatial point $x_B^i$ is imaged by the x-ray cone.

There are then one or more coordinate system transformations $T_W(B^i, B^j)$, which describe the change in the three-dimensional position of the image intensifier from the position at the time of recording an image i to the position at the time of recording another image j in a coordinate system of the world W (this is for example the system of a spatially fixed camera or usually the reference star system which is connected to the object to be imaged):

$$E_W^j = T_W(B^i, B^j) \cdot E_W^j$$

wherein $E_W^i, E_W^j$ are the 3D image planes with respect to different x-ray recordings in the common global coordinate system. The transformation $T_W(B^i, B^j)$ can for example be compiled from the transformations of the position of the image converter at the times of the recordings $B_W^i, B_W^j$ into the origin of the global coordinate system:

$$T_W(B^i, B^j) = (T_{B_W^i \to O_W})^{-1} \cdot T_{B_W^j \to O_W}$$

The transformations described above can for example be classic 3×4 translation-rotation matrices or also for example the 4×4 matrices common in computer graphics, with additional scaling information.

If one image (once rectified and registered) is displayed as the preferred orientation of a plane in coordinates of the computer graphics system (for example, in the vertex coordinate system of openGL), the same transformation $T_W(B^i, B^j)$ can be used to orient the second image in the sense of the invention and to display it such that it is oriented and scaled with respect to the first image by means of the computer graphics system:

$$E_V^j = T_V(B^i, B^j) \cdot E_V^j$$

To this end, one plane (for example, the first plane) is expediently displayed such that it is oriented parallel to the monitor, and initially scaled such that several or all of the recordings to be displayed can be displayed on the screen to the correct scale and at the correct distance. To this end, the distance to the next image is for example calculated in units of the image width of one image, and the scale is chosen in the following way: scale=(maximum width which can be displayed on the screen, in pixels)/(maximum image width in units X+maximum central distance to another image in units X).

In order to prepare additional image information and/or orientation information for a surgeon and/or physician, it is preferred—after a first and second recording have been produced in accordance with the invention—for the x-ray apparatus to be moved into a different position, in which to again record at least two recordings in accordance with the method in accordance with the invention at a different angle to the region to be imaged, wherein it is particularly advantageous if the second set of a first recording and second recording have been acquired at a particular angle, preferably 90°, to the first set of a first recording and second recording, since optimized spatial image information can thus be obtained. The respectively overlapping recordings of the two sets of recordings which may be distanced from each other and/or are recorded at an angle to each other can then be registered and oriented with respect to each other in accordance with the invention, in order to be combined to form a cohesive image on one or more screens, wherein spatial assignments between the image information of the x-ray recordings are computationally produced by means of the stereo camera and the markers detected by it.

Both aspects of the invention also of course include programs which realize the method in accordance with the invention, and data carriers which digitally store corresponding programs for executing on a computer for realizing the method in accordance with the invention.

BRIEF DESCRIPTION OF THE DRAWINGS

The present invention is described below in more detail on the basis of a preferred embodiment and by referring to the enclosed drawings, wherein additional features, preferences and aims in accordance with the invention are disclosed.

DETAILED DESCRIPTION

Figure 1A:
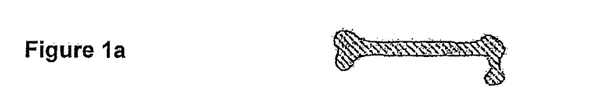
FIGS. 1a to 1c show an anatomical structure (FIG. 1a), which has been recorded such that it does not overlap, and which on the one hand is displayed such that it is oriented and correctly scaled (FIG. 1b), and on the other hand is recorded and depicted in an overlapping representation in accordance with the invention (FIG. 1c).

FIG. 1a shows an anatomical structure in the form of a human femur. This anatomical structure is then to be recorded by means of an x-ray apparatus, in particular a so-called C-arm, and the radioscopic images thus produced are to be depicted so as to enable the observer to derive the greatest possible use from the prepared image information, i.e. the image contents displayed have to be exact, match each other and where possible be mutually adapted in relation to their measurements, dimensions, angles, etc., or at least be made to be identifiable.

Figure 1B:
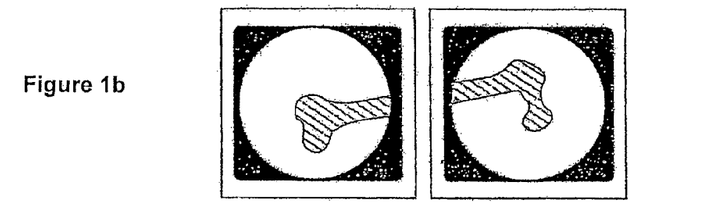

If the x-ray recordings are for example depicted in two display regions, it is possible—as shown in FIG. 1b—to register the two image contents of the two recordings which the x-ray apparatus has taken, on the basis of which the observer can navigate. A comparison with FIG. 3 makes the difference with respect to the prior art immediately clear. While a registered representation of the image contents is produced in accordance with the invention, wherein the image contents match each other with respect to their measurements, magnifications, etc., an exact orientation on the basis of the images in accordance with the prior art cannot be claimed (see FIGS. 1a, 3).

Figure 1C:
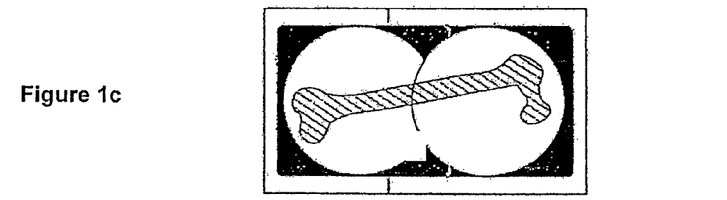

A representation corresponding to FIG. 1b is visualized in accordance with FIG. 1c, in which the two recordings—as also imaged in two display regions in accordance with FIG. 1b—are displayed in an immediately consecutive way in accordance with the invention, such that it can be seen that the recordings which are recorded and/or depicted in accordance with the invention overlap, wherein an image region of one recording can provide the overlap region which is overlapped with an image region of the other recording, such that the anatomical partial structure displayed in the left-hand screen content is seamlessly joined to the partial structure in the right-hand screen content.

Figure 2:
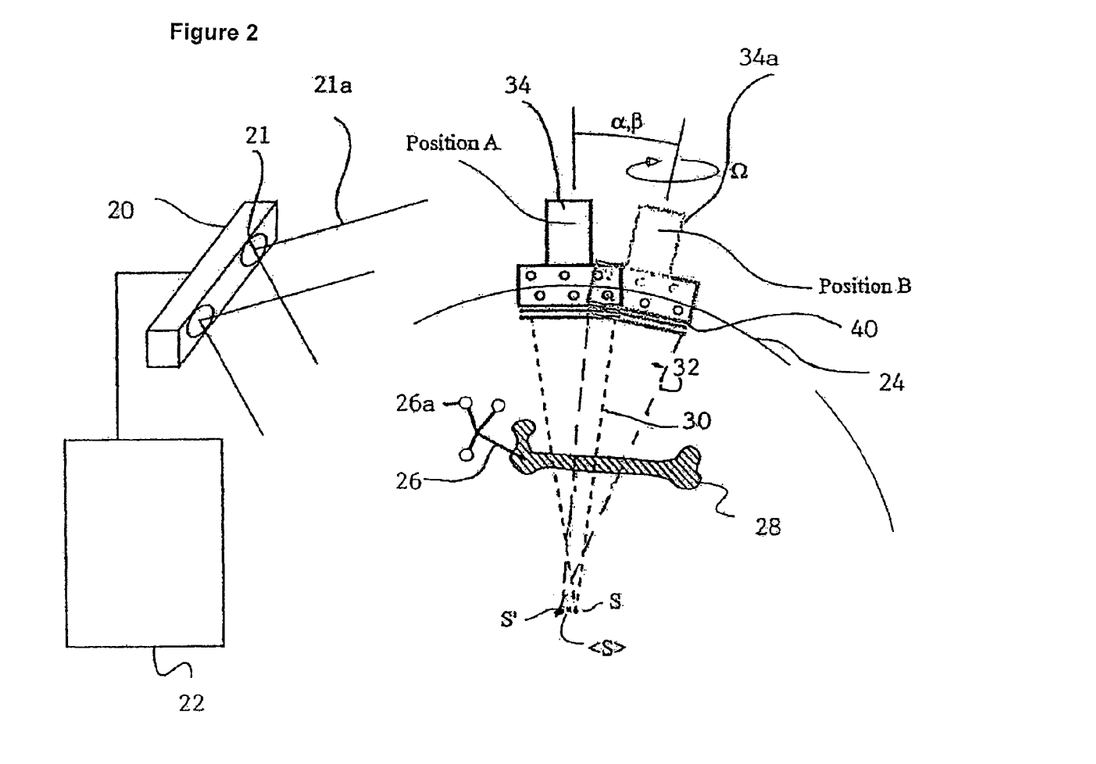
FIG. 2 shows a recording array for performing the method in accordance with the invention, and/or a variant of the same.
Figure 5:
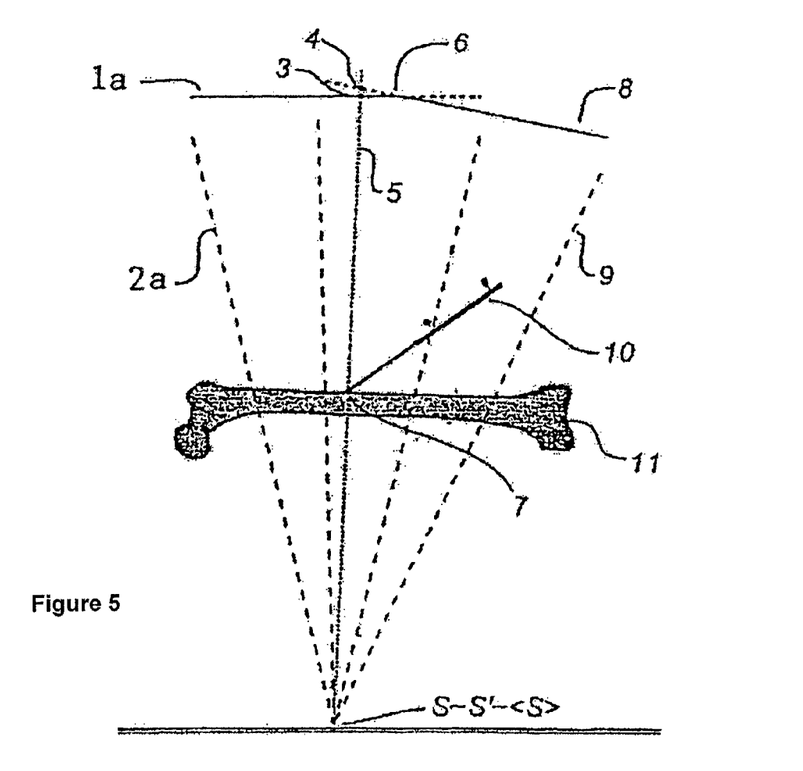
FIG. 5 shows a partially shown method sequence for registering two recordings of a region to be imaged.

FIGS. 2 and 5 show the principle construction of a navigated x-ray recording system such as could be used to perform the method in accordance with the present invention. FIG. 2 shows a principle representation of a navigation system which among other things comprises a stereo camera 20 comprising a pair of object lenses 21. The stereo camera is connected to a data processing system 22. The object lenses 21 of the stereo camera—for example, an infrared stereo camera—exhibit respective detection angles 21a and/or corresponding detection ranges within which the existence of markers 26a can be detected and positionally processed.

Markers 26a are provided on an x-ray detector 34 or on another object which has a known geometry and on which x-ray markers are situated and which is situated in the radiation path (not shown). A recording cone 30 extends between the x-ray detector 34 and the x-ray source S, within which an object 28 to be imaged—in this case, a femur 28—is to be detected and imaged using one or more x-ray recordings. Multiple markers 26a, in the form of a marker kit 26 comprising multiple markers 26a, are likewise arranged positionally fixed on the femur 28.

A calibration array 40 can be arranged on the x-ray detector 34 for the purpose of image rectifying and registering.

Changes in the position of both the source and the x-ray detector can likewise be ascertained mechanically and/or electromagnetically. Inductively functioning sensors can for example be used, or incremental encoders can output clock pulses in any spatial directions, which can likewise be adduced in accordance with the invention for corresponding image processing.

Since the principle functionality of such an x-ray apparatus in conjunction with a navigation system has already been illustrated above, reference is merely made to this.

In the representation in accordance with FIG. 2, it is then provided for that the x-ray detector 34 is moved along a spherical shell 24 relative to the femur 28, into another position which is indicated by the reference sign 34a. While in the first position A, the x-ray detector 34 exhibits the imaging cone 30 which is predetermined by the opposing x-ray source S; in the second position B (indicated as 34a) for recording a second x-ray recording, the x-ray detector 34 has a projection cone 32, at the pointed end of which the x-ray source S', which has been spatially offset slightly, lies. The x-ray source S corresponds of course to the x-ray source S', but is slightly spatially offset by the x-ray detector 34 being moved to the position B. The x-ray source S would ideally be situated at the same location after the x-ray detector has been moved into the position B, however this would be difficult to enable in practice. The angles $\alpha$ and $\beta$ describe the change in angle between the straight connecting line defined by the x-ray source S and the x-ray detector in the position A and the straight connecting line defined by the position S' of the x-ray source and the x-ray detector 34 in its position B. For example, $\alpha$ corresponds to a change in angle in the plane of the sheet and $\beta$ corresponds to a change in angle perpendicular to this. The angle $\Omega$ corresponds to a rotation of the x-ray detector about the axis created by the straight connecting line between the x-ray detector 34, 34a and the x-ray source S, S'.

When the x-ray detector is moved out of the position A into the position B, the position of the x-ray source S remains near to this position and is merely moved into a slightly deviating position S'. From this, an average position of the x-ray source <S> can be ascertained, or another suitable position near the averaged position. Using this position <S>, it is possible to produce a definitive imaging protocol using which all the image points which have been recorded in the position A and all the image points which have been recorded in the position B can be jointly imaged such that they are oriented and coordinated with respect to each other and true-to-scale, wherein the resultant inaccuracy for navigation can for example be determined by purely geometric considerations and/or calculations which can also be made by the data processing for navigation, or by comparing markers which are detected in the image and have a known geometry with the theoretical position originating from registration, and can then for example be displayed to the user and/or used in order to accept or reject the second recording in the sense of this method.

The method variants specified in the present disclosure have in particular in common that, by using imaging cones between the x-ray sources and the x-ray detectors which can be correlated with each other, the ascertained image data of the two or more images can be processed by a common imaging protocol with a minimum of error, in order to provide them on one, two or any number of screen sections or screens, such that they are oriented with respect to each other, match in terms of their scale and comprise other orientation aids for an operator, for instance a surgeon.

By using the Applicant's software which is known in the prior art by the name "MEPUC", it is possible to record recordings of a region to be imaged within tolerable limits which are to be determined. This software and these illustrations are known to the person skilled in the art, but shall again be definitively incorporated into the present disclosure here by reference.

Referring to FIG. 5, a region to be imaged 11 is projected onto the image plane 1a from S and onto the image plane 8 from S' within the overlap region of x-ray cones 2a, 9, wherein a navigated depiction is produced in the imaging plane spanned by the image planes or images 1a, 8, wherein a differentiable image point 7 of an object—in this case, the tip of a pointing instrument (pointer)—can for example be projected along a ray 5 from <S> onto points 3 and 4 in the corresponding imaging planes. An oriented depiction can be compiled from the image 1 up to the point of intersection 6, and thence from the image 8, or the respectively dotted part of the images 1a, 8 is projected along the central rays onto the non-dotted parts, where the image information which respectively exhibits 50% transparency or attenuation is summed, in order to take account of the fact that the projections are slightly shifted (for example, by less than 1 mm) with respect to each other. The common coordinate system is spanned on the basis of the assumption that <S> is the common centre of projection or symmetry.

Objects which are recorded with an imperfect overlap of S and S' may contain a slightly diffuse edge and/or blurred zones, since they are projected onto slightly different locations of the panorama image for the oriented depiction. This diffuse edge is a good optical indication of the reduced accuracy.

If a defined part of the image is respectively used, it is also possible to calculate the image information and the position of a navigated tool in the panorama image of the region to be imaged both from S and from S', and to display the image information and the tool merely in the overlap region, averaged in relation to <S>, correspondingly with a slightly magnified, blurred or distorted contour.

The two depiction methods just described also in particular work when the x-ray cones do not overlap. The region between the images can then for example be displayed in black, as follows in principle from FIG. 1b. In this case, the position of navigated tools can always be calculated from the exact positions of the centers of projection. The distance, scale and orientation of the depictions with respect to each other follow from the position of <S>, the common centre.

In accordance with the invention, it is also possible to combine more than two images, in particular if the x-ray detector is situated on a spherical shell about S, the x-ray source, when a recording is taken. This spherical shell is then converted or transformed using a projection onto the 2D plane of the monitor. Such depictions can also be produced in other coordinate systems. What is essential is that the x-ray source lies near or in the centre of symmetry of the coordinate system, and a definitive imaging function exists, using which the image points of the x-ray recordings to be joined together can be mutually adapted.

Using the methods described by referring to FIGS. 2 and 5, a set of recordings comprising a first and second x-ray recording can be produced. A second set comprising a first and second x-ray recording can subsequently be produced in accordance with the invention. The position of the straight connecting line from <S> to the centre point of all the detector positions used for the first set can then be recorded at an angle, in particular 90°, to the corresponding straight connecting line of the second set and/or distanced with respect to the corresponding straight connecting line of the second set. Via marker positions stored by the stereo camera when the respective recording sets are produced, it is then possible to linearly correlate the image information of the recording sets. It is of course also correspondingly possible to produce additional sets of two or more x-ray recordings and orient and/or register them with respect to each other, in order to depict them such that they are overlapped on one or more screens.

Figure 4:
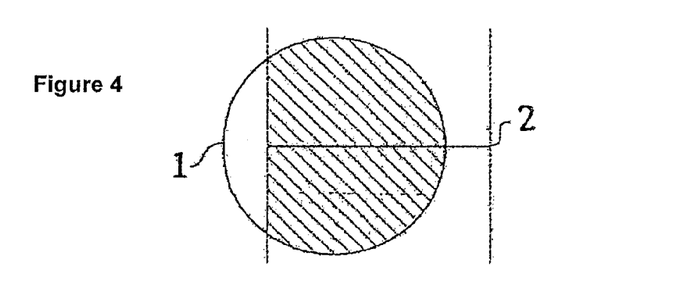
FIG. 4 schematically shows two recordings for navigation, displayed such that they overlap, in accordance with the prior art, wherein the recording planes are substantially perpendicular to each other.

Overall, it is possible in accordance with the invention and its embodiments to very greatly increase the region which can be used in particular for three-dimensional navigation, i.e. in particular the region which follows from FIG. 4.

Figure 6A:
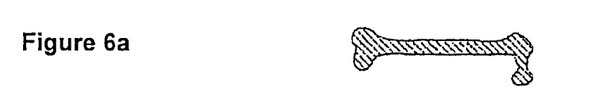
FIGS. 6a and 6b show an anatomical structure (FIG. 6a), which has been recorded such that it does not overlap, and which is oriented and scaled in accordance with the invention (FIG. 6b).

FIG. 6a shows an anatomical structure in the form of a human hip bone. This anatomical structure is then to be recorded by means of an x-ray apparatus, in particular a so-called C-arm, and the radioscopic images thus produced are to be depicted so as to enable the observer to derive the greatest possible use from the prepared image information, i.e. the image contents displayed have to be exact, match each other and where possible be mutually adapted in relation to their measurements, dimensions, angles, etc., or at least be made to be identifiable.

Figure 6B:
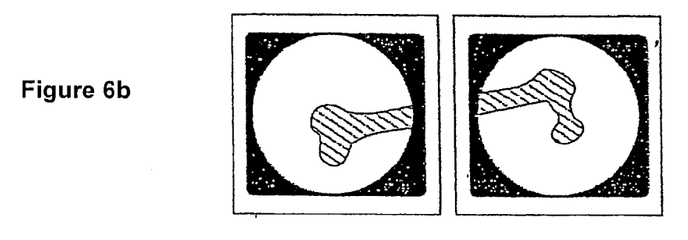

If the x-ray recordings are for example depicted in two display regions, it is possible—as shown in FIG. 6b—to register the two image contents of the two recordings which the x-ray apparatus has taken, on the basis of which the observer can navigate without problems. A comparison with FIG. 3 makes the difference with respect to the prior art immediately clear. While a registered representation of the image contents is produced in accordance with the invention, wherein the image contents match each other with respect to their measurements, magnifications, etc., an exact orientation on the basis of the images in accordance with the prior art cannot be claimed (see FIG. 3).

Figure 7:
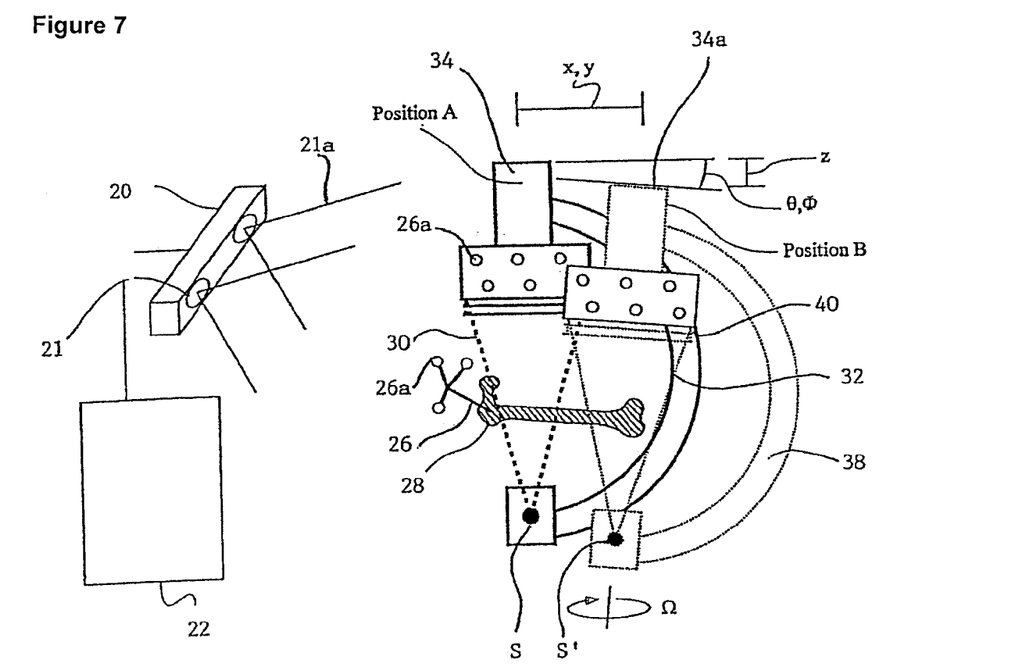
FIG. 7 shows a recording array for performing the method in accordance with the invention, and/or a variant of the same; the translations by x, y and z and the rotations by $\Omega$, $\Theta$ and $\phi$ define the transformation $T_W(B^i, B^j)$; in this case, i=position A, j=position B and the reference star 26a defines W.

FIG. 7 shows the principle construction of a navigated x-ray recording system such as could be used to perform the method in accordance with the present invention. FIG. 7 shows a principle representation of a navigation system which among other things comprises a stereo camera 20 comprising a pair of object lenses 21. The stereo camera is connected to a data processing system 22. The object lenses 21 of the stereo camera—for example, an infrared stereo camera—exhibit respective detection angles 21a and/or corresponding detection ranges within which the existence of markers 26a can be detected and positionally processed.

Markers 26a are provided on an x-ray detector 34, 34a. The x-ray detector 34 lies opposite an x-ray source S, S'. A recording cone 30, 32 extends between the x-ray detector 34 and the x-ray source S, S', within which an object 28 to be imaged—in this case, a femur 28—is to be detected and imaged using one, in particular two or more, x-ray recordings. Multiple markers 26a, in the form of a marker kit 26 comprising multiple markers 26a, are likewise arranged positionally fixed on the femur 28.

A calibration array 40 is arranged on the x-ray detector 34 for the purpose of calibration.

The principal functionality of such an x-ray apparatus in conjunction with a navigation system begins, in accordance with the method in accordance with the invention, with producing a first recording of the region to be imaged from a first position using the x-ray apparatus, wherein a first control signal is output. Conversely, the navigation device can detect the initiating of the recording via an image analysis and output a first control signal. The first control signal causes the stereo recording system 20, 21 to detect first positions of the multiple marker devices 26a on the x-ray detector and the region to be imaged.

The data concerning the first positions of the marker devices 26a is stored and correlated, with computer assistance, with image points of the first x-ray recording, in order to register the x-ray recording. The x-ray detector is then moved, together with the x-ray source S, S', relative to the region to be imaged into a second position S' and a second recording is initiated by the x-ray detector, wherein a second control signal is output. The second control signal causes the stereo recording system 20, 21 to detect second positions of the marker devices 26a on the x-ray detector and the region to be imaged.

Figure 9:
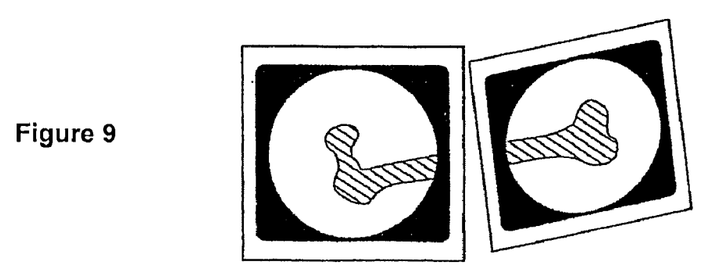
FIG. 9 shows depicting two x-ray recordings in a correlated way in accordance with the invention.

The data concerning the second positions of the marker devices 26a is then correlated, with computer assistance, with image points of the x-ray recording, in order to register the second x-ray recording. Via the common coordinate system of the region to be imaged, a transformation matrix for the change in the position of the detector 34 between the first recording in accordance with the position A in FIG. 7 and the second recording in accordance with the position B in FIG. 7 is determined. By means of a matrix based on this, the recordings are oriented and scaled with respect to each other, wherein the true-to-scale scale of magnitude is ascertained from the change in position in the z direction, the true-to-scale distance between the images is ascertained from a change in position in the x and/or y direction, the true-to-scale rotation is ascertained from an angle $\Omega$, and the true-to-scale tilt of the second recording with respect to the plane of the first recording is ascertained from angles $\Theta$ and $\phi$. The two recordings are then displayed, such that they are oriented with respect to each other, on one or more screens, as follows for instance from FIG. 9, wherein two recordings are advantageously produced in at least approximately the same plane.

In accordance with FIG. 7, the x-ray detector 34—which is mounted on a C-arm 38 and opposite which the x-ray source S is arranged on the C-arm—is moved in its position in any way, in order on the one hand to produce an x-ray recording from the position A and on the other hand to produce an x-ray recording from the position B. The position of navigated tools can always be calculated from the exact positions of the centers of projection and indicated on the displayed images.

The depiction method just described also in particular works when the x-ray cones do not overlap. The region between the images can then for example be displayed in black. If the images do overlap, it is desirable in the representation of navigated tools to differentiate the ray projections which the tool representations relate to. If there is an overlap, it may for example only be possible to display a tool in the front (or rear) part of the image (for the observer) or even twice (along both ray projections). In the latter case, the tool representation is expediently marked in such a way that it is clear which image it relates to (for example, by coloration).

In accordance with the invention, it is also possible to combine more than two images.

Figure 10:
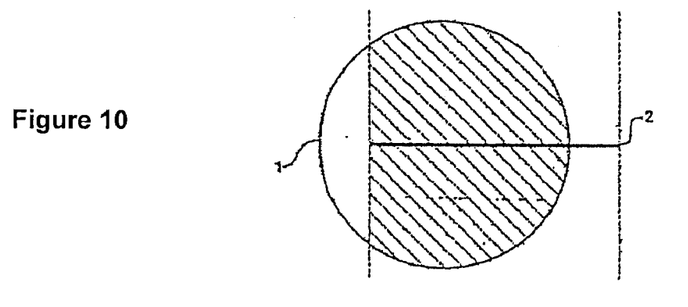
FIG. 10 schematically shows two recordings for navigation, displayed such that they overlap, in accordance with the prior art, wherein the recording planes are substantially perpendicular to each other.

Using the methods described by referring to FIGS. 7 and 10, a set of recordings comprising a first and second x-ray recording can be produced. A second set comprising a first and second x-ray recording can subsequently be produced in accordance with the invention. The general orientation of the first set can then be recorded at an angle, in particular 90°, to the general orientation of the second set and/or distanced with respect to the general orientation of the second set. It is of course also correspondingly possible to produce additional sets of two or more x-ray recordings and orient and/or register them with respect to each other, in order to depict them such that they are overlapped on one or more screens.

Overall, it is possible in accordance with the invention and its embodiments to very greatly increase the region which can be used in particular for three-dimensional navigation, i.e. in particular the region which follows from FIG. 10.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for the oriented depiction of recordings of a region to be imaged which is recorded in at least two recording steps using a navigation system comprising the following features:
    an x-ray device comprising an x-ray detector and an x-ray source arranged opposite to the x-ray detector, the x-ray detector and x-ray source movable with respect to each other and with respect to the region to be imaged;
    a stereo recording system;
    marker devices assigned to the x-ray detector and the region to be imaged, said marker devices at least partially detectable by the stereo recording system;
wherein the method comprises the following steps:
    a) initiating a first recording of a first portion of the region to be imaged when the x-ray source and x-ray detector are in a first position, said initiating the first recording including outputting a first control signal;
    b) based on the first control signal, the stereo recording system detecting first marker positions of the marker devices on the x-ray detector and the region to be imaged;
    c) storing data concerning the first marker positions;
    d) correlating, with computer assistance, the data concerning the first marker positions with image points of the x-ray recording in order to register the x-ray recording;
    e) ascertaining and storing a first position of the x-ray source relative to the detector;
    f) determining, with the aid of the registration, the position of the x-ray source in the coordinate system of the region to be imaged, and storing the determined position of the x-ray source;
    g) moving the x-ray detector and the x-ray source relative to the region to be imaged into a second position for a second recording, wherein changes in the position of the x-ray detector are detected during the movement, and a second position of the x-ray source is determined by means of the first relative position;
    h) initiating a second recording of a second portion of the region to be imaged when the x-ray source and x-ray detector are in the second position, said second portion axially shifted relative to said first portion, and wherein said initiating the second recording includes outputting a second control signal;
    i) based on the second control signal, the stereo recording system detecting second marker positions of the marker devices on the x-ray detector and the region to be imaged;
    j) correlating, with computer assistance, the data concerning the second marker positions with image points of the x-ray recording in order to register the second x-ray recording;
    k) ascertaining an additional position from the second position and the first position;
    l) based on the additional position, registering and displaying the recordings in a superimposed way.

2. The method according to claim 1, wherein the recordings of the region to be imaged are overlapping recordings.

3. The method according to claim 1, wherein the recordings of the region to be imaged are recordings of an anatomical structure.

4. The method according to claim 1, wherein the changes in the position of the detector are mechanically determined or determined by the navigation system.

5. The method according to claim 1, wherein step k) includes determining a difference between the first and second positions of the x-ray source.

6. The method according to claim 5, further comprising determining whether the difference exceeds a maximum value for the difference.

7. The method according to claim 1, wherein a common position is calculated by spatial averaging or by weighted calculation and/or averaging.

8. The method according to claim 6, wherein the second and/or subsequent recording is suppressed or repeated if the difference exceeds the maximum value for the difference.

9. The method according to claim 1, wherein the x-ray detector is moved such that the second position is equal to or similar to the first position of the x-ray detector.

10. The method according to claim 1, wherein based on a first calculated source position of the x-ray source the stereo recording system ascertains for the first recording the positioning steps which the x-ray detector undergoes in order to arrive at a second source position of the x-ray source for producing the second recording, wherein the second source position is different from the first source position.

11. The method according to claim 1, wherein positioning steps are displayed to an operator by means of a display device.

12. The method according to claim 10, wherein the x-ray device comprises a motorized actuator which, via automatic or manual control, implements the positioning steps.

13. The method according to claim 1, wherein subsequent x-ray recordings are taken from other positions and incorporated in an adapted form with the first x-ray recording or with an overall representation produced on the basis of the first x-ray recording.

14. The method according to claim 1, wherein a first set of recordings comprising the first recording and second recording is produced relative to a first common position, and a second set of recordings which contains another first recording and second recording is produced in a second common position which is different to the first common position, wherein the common positions are rotated by an angle with respect to each other and/or distanced from each other.

15. The method according to claim 14, wherein the angle exceeds a minimum value which is at least 30°.

16. The method according to claim 15, wherein the minimum value is at least 60°.

17. The method according to claim 15, wherein the minimum value is at least 90°.

18. The method according to claim 1, wherein the control signals are produced by the x-ray apparatus or the navigation system on the basis of an image analysis.

19. A method for the oriented depiction of recordings of a region to be imaged which is recorded in at least two recording steps using a navigation system, wherein the recordings are localizable in a common coordinate system of the region to be imaged, wherein the navigation system comprises the following features:
 an x-ray device comprising an x-ray detector and an x-ray source arranged opposite to the x-ray detector, the x-ray detector and x-ray source movable with respect to each other and with respect to the region to be imaged;
 a stereo recording system;
 marker devices assigned to the x-ray detector and the region to be imaged, said marker devices at least partially detectable by the stereo recording system;
wherein the method comprises the following steps:
 a) initiating a first recording of a first portion of the region to be imaged when the x-ray source and x-ray detector are in a first position, said initiating the first recording including outputting a first control signal;
 b) based on the first control signal, the stereo recording system detecting first positions of the marker devices on the x-ray detector and the region to be imaged;
 c) storing data concerning the first positions;
 d) correlating, with computer assistance, the data concerning the first positions with image points of the x-ray recording in order to register the x-ray recording;
 e) moving the x-ray detector and the x-ray source into a second position relative to the region to be imaged;
 f) initiating a second recording of a second portion of the region to be imaged when the x-ray detector and x-ray source are in the second position, wherein said initiating the second recording includes outputting a second control signal;
 g) based on the second control signal, the stereo recording system detecting second positions of the marker devices on the x-ray detector and the region to be imaged;
 h) correlating, with computer assistance, data concerning the second positions with image points of the x-ray recording in order to register the second x-ray recording;
 i) via a common coordinate system of the region to be imaged, determining a transformation matrix for the change in the position of the x-ray detector between the first and second recordings;
 j) orienting and scaling the recordings with respect to each other using the matrix, wherein a true-to-scale scale of magnitude is determined from the change in position in the z direction, a true-to-scale distance between the recordings is determined from a change in position in the x and/or y direction, a true-to-scale rotation is determined from an angle $\Omega$, and a true-to-scale tilt of the second recording with respect to the plane of the first recording is determined from angles $\Theta$ and $\phi$;
 k) displaying the oriented and scaled recordings with respect to each other using at least one of the true-to-scale scale of magnitude, true-to-scale distance, true-to-scale rotation, and true-to-scale tilt.

20. The method according to claim 19, wherein the recordings of the region to be imaged are recordings of an anatomical structure.

21. The method according to claim 19, wherein the control signals are produced by the x-ray apparatus or the navigation system on the basis of an image analysis.

22. The method according to claim 19, wherein subsequent x-ray recordings are taken from other positions and incorporated in an adapted form with the first x-ray recording or with an overall representation produced on the basis of the first x-ray recording.

23. The method according to claim 19, wherein a first set of recordings comprising the first recording and second recording is produced relative to a first common position, and a second set of recordings which contains another first recording and second recording is produced in a second common position which is different to the first common position, wherein the common positions are rotated by an angle with respect to each other and/or distanced from each other.

24. The method according to claim 23, wherein the angle is about 90°.

25. The method according to claim 19, wherein possible positioning steps are displayed to an operator by means of a display device.

26. The method according to claim 19, wherein the recording array comprises a motorized array which, via automatic or manual control, implements desired positioning steps to place the x-ray detector and the x-ray source in the at least one of the first and second positions.

27. The method according to claim 19, wherein said second portion is axially shifted relative to said first portion.

28. A computer program stored on a machine-readable medium for the oriented depiction of recordings of a region to be imaged which is recorded in at least two recording steps using a navigation system comprising the following features:
an x-ray device comprising an x-ray detector and an x-ray source arranged opposite the x-ray detector, the x-ray detector and x-ray source movable with respect to each other and with respect to the region to be imaged;
a stereo recording system;
marker devices assigned to the x-ray detector and the region to be imaged, said marker devices at least partially detectable by the stereo recording system;
wherein the computer program comprises:
code which initiates a first recording of a first portion of the region to be imaged when the x-ray source and x-ray detector are in a first position, wherein a first control signal is output;
code which based on the first control signal causes the stereo recording system to detect first marker positions of the multiple marker devices on the x-ray detector and the region to be imaged;
code which stores data concerning the first marker positions;
code which correlates the data concerning the first marker positions with image points of the x-ray recording in order to register the x-ray recording;
code which ascertains and stores a first position of the x-ray source relative to the detector;
code which determines, with the aid of the registration, the position of the x-ray source in the coordinate system of the region to be imaged, and stores the determined position of the x-ray source;
code which causes the x-ray detector and the x-ray source to be moved into a second position relative to the region to be imaged for a second recording, wherein changes in the position of the detector are detected during the movement, and a second position of the source is determined by means of the first relative position;
code which initiates a second recording of a second portion of the region to be imaged when the x-ray source and x-ray detector are in the second position, said second portion axially shifted relative to said first portion, and wherein a second control signal is output;
code which based on the second control signal causes the stereo recording system to detect second marker positions of the marker devices on the x-ray detector and the region to be imaged;
code which correlates the data concerning the second marker positions with image points of the x-ray recording, in order to register the second x-ray recording;
code which ascertains an additional position from the second position and the first position;
code which based on the additional position registers and displays the recordings in a superimposed way.

29. A computer program stored on a machine-readable medium for the oriented depiction of recordings of a region to be imaged which is recorded in at least two recording steps using a navigation system, wherein the recordings are localizable in a common coordinate system of the region to be imaged, wherein the navigation system comprises the following features:
an x-ray device comprising an x-ray detector and an x-ray source arranged opposite to the x-ray detector it, the x-ray detector and x-ray source movable with respect to each other and with respect to the region to be imaged;
a stereo recording system;
marker devices assigned to the x-ray detector and the region to be imaged, said marker devices at least partially detectable by the stereo recording system;
wherein the computer program comprises:
code which initiates a first recording of a first portion of the region to be imaged when the x-ray source in a first position, wherein a first control signal is output;
code which based on the first control signal causes the stereo recording system to detect first positions of the multiple marker devices on the x-ray detector and the region to be imaged;
code which stores data concerning the first positions;
code which correlates the data concerning the first positions with image points of the x-ray recording in order to register the x-ray recording;
code which causes the x-ray detector and the x-ray source to be moved into a second position relative to the region to be imaged;
code which initiates a second recording of a second portion of the region when the x-ray source and x-ray detector are in the second position, wherein a second control signal is output;
code which based on the second control signal causes the stereo recording system to detect second positions of the marker devices on the x-ray detector and the region to be imaged;
code which correlates data concerning the second positions with image points of the x-ray recording, in order to register the second x-ray recording;
code which determines, via a the common coordinate system of the region to be imaged, a transformation matrix for the change in the position of the x-ray detector between the first and second recordings;
code which orients and scales the recordings with respect to each other using the matrix, wherein a true-to-scale scale of magnitude is determined from the change in position in the z direction, a true-to-scale distance between the recordings is determined from a change in position in the x and/or y direction, a true-to-scale rotation is determined from an angle $\Omega$, and a true-to-scale tilt of the second recording with respect to the plane of the first recording is determined from angles $\Theta$ and $\phi$;
code which displays the oriented and scaled recordings with respect to each other using at least one of the true-to-scale scale of magnitude, true-to-scale distance, true-to-scale rotation, and true-to-scale tilt.

30. A method of displaying image data for an object, comprising:
obtaining first image data for a first portion of the object from a first direction;
obtaining second image data for a second portion of the object from a second direction different from the first direction, said first portion of the object being axially spaced apart from said second portion of the object;
registering the first image data to the second image data such that an orientation and dimension of the first portion of the object as represented in the first image data corresponds to an orientation and dimension of the object as represented in the second image data; and
displaying the first image data and the second image data.

* * * * *